(12) United States Patent
Aono et al.

(10) Patent No.: US 7,969,067 B2
(45) Date of Patent: Jun. 28, 2011

(54) ULTRASOUND PROBE

(75) Inventors: Takanori Aono, Hitachinaka (JP);
Tatsuya Nagata, Ishioka (JP);
Katsunori Asafusa, Kashiwa (JP);
Takashi Kobayashi, Nagareyama (JP);
Naoya Kanda, Fujisawa (JP)

(73) Assignee: Hitachi Medical Corporation, Tokyo (JP)

( * ) Notice: Subject to any disclaimer, the term of this patent is extended or adjusted under 35 U.S.C. 154(b) by 159 days.

(21) Appl. No.: 12/161,962

(22) PCT Filed: Nov. 14, 2006

(86) PCT No.: PCT/JP2006/322649
§ 371 (c)(1),
(2), (4) Date: Jul. 24, 2008

(87) PCT Pub. No.: WO2007/086180
PCT Pub. Date: Aug. 2, 2007

(65) Prior Publication Data
US 2009/0069688 A1 Mar. 12, 2009

(30) Foreign Application Priority Data
Jan. 26, 2006 (JP) .................................. 2006-017137

(51) Int. Cl.
*H01L 41/08* (2006.01)
(52) U.S. Cl. ...................................................... 310/334
(58) Field of Classification Search .................. 310/334, 310/335, 336, 320, 322, 328, 365, 326, 364; 361/329; *H01L 41/08*
See application file for complete search history.

(56) References Cited

U.S. PATENT DOCUMENTS

| | | | | |
|---|---|---|---|---|
| 5,870,351 A | * | 2/1999 | Ladabaum et al. | 367/163 |
| 5,894,452 A | * | 4/1999 | Ladabaum et al. | 367/163 |
| 5,974,884 A | | 11/1999 | Sano et al. | |
| 6,295,247 B1 | * | 9/2001 | Khuri-Yakub et al. | 367/140 |
| 6,714,484 B2 | | 3/2004 | Ladabaum et al. | |
| 2004/0190377 A1 | | 9/2004 | Lewandowski et al. | |
| 2005/0275313 A1 | | 12/2005 | Yamashita et al. | |

(Continued)

FOREIGN PATENT DOCUMENTS

EP 1 671 589 6/2006

(Continued)

OTHER PUBLICATIONS

Japanese Office Action, dated Dec. 7, 2010, issued in corresponding Japanese Patent Application No. 2006-017137.

*Primary Examiner* — Walter Benson
*Assistant Examiner* — Karen Addison
(74) *Attorney, Agent, or Firm* — Antonelli, Terry, Stout & Kraus, LLP.

(57) ABSTRACT

There is provided an ultrasound probe including a first substrate having a silicon substrate and an ultrasound transmit-receive element, an acoustic lens disposed over an upper surface of the first substrate, and a damping layer disposed under the first substrate, in which a second substrate is disposed between a lower surface of the first substrate and an upper surface of the damping layer, and the second substrate is made of a material having approximately the same linear expansion coefficient and acoustic impedance as the silicon substrate of the first substrate. With this structure, it is possible to provide the ultrasound probe which can prevent damage to the silicon substrate due to temperature change and has excellent transmission/reception performance and structure reliability while reducing noise by reflected waves in transmission and reception.

5 Claims, 3 Drawing Sheets

U.S. PATENT DOCUMENTS

2006/0004290 A1  1/2006  Smith et al.

FOREIGN PATENT DOCUMENTS

| | | |
|---|---|---|
| JP | 62-115197 | 5/1987 |
| JP | 63-159750 | 7/1988 |
| JP | 02-032284 | 2/1990 |
| JP | 2000-165995 | 6/2000 |
| JP | 2001-048668 | 2/2001 |
| JP | 2002-112393 | 4/2002 |
| JP | 2005-086458 | 3/2005 |
| JP | 2005-295553 | 10/2005 |
| JP | 2006-033801 | 2/2006 |
| WO | WO 03/000337 | 1/2003 |
| WO | WO 2005/032374 | 4/2005 |

* cited by examiner

ULTRASOUND PROBE

FIELD OF THE INVENTION

The present invention relates to an ultrasound probe for transmitting and receiving ultrasound waves.

DESCRIPTION OF THE RELATED ART

As a conventional ultrasound probe which is applied in a field where a subject is tested with ultrasound waves, there is contrived an ultrasound probe in which a transmit-receive element is composed of a gap, an insulating layer, and an electrode on a silicon substrate and a damping layer having an acoustic impedance matched to the silicon substrate is disposed on the other side of the silicon substrate. The ultrasound probe has the function of applying a DC voltage (bias voltage) between the electrode and the silicon substrate to shorten the gap to a predetermined position and applying an AC voltage (drive voltage for transmitting an ultrasound wave) between the electrode and the silicon substrate to expand and contract the gap, thereby transmitting an ultrasound wave. The ultrasound probe also has the function of detecting a change in capacitance between the electrode and the silicon substrate by an ultrasound wave reflected from a test body, thereby receiving the ultrasound wave. The damping layer has the function of reducing the reflection of ultrasound waves in transmission and reception. More specifically, the damping layer is made of a material having an acoustic impedance matched to the silicon substrate by mixing tungsten particles into epoxy resin. For example, U.S. Pat. No. 6,714,484B2 pertains to this conventional technology.

In the ultrasound probe for transmitting and receiving ultrasound waves by electrostatic drive, an ultrasound transducer needs to be formed with high density; accordingly, the ultrasound probe is manufactured by microfabrication through the use of semiconductor manufacturing technology and MEMS (Micro Electro Mechanical Systems) technology. In these microfabrication technologies, silicon is used for a base substrate. In the ultrasound probe, it is necessary to match the acoustic impedances between the silicon substrate and the damping layer in order to reduce the reflection of ultrasound waves in transmission and reception. For this reason, in U.S. Pat. No. 6,714,484B2, the damping layer is made of a material obtained by mixing a proper quantity of tungsten particles into epoxy resin, in order to match the acoustic impedances of the base substrate and the damping layer. In this case, although it is possible to match the acoustic impedances of the base substrate and the damping layer, there is a difference in linear expansion coefficient between the base substrate and the damping layer; therefore, there is a problem that the structure reliability is so insufficient that the base substrate may be destroyed due to deformation with temperature change.

SUMMARY OF THE INVENTION

It is an object of the present invention to provide an ultrasound probe which can prevent damage to the silicon substrate due to temperature change and has excellent transmission/reception performance and structure reliability.

In order to attain the above object, the present invention provides an ultrasound probe including a first substrate having a silicon substrate and an ultrasound transmit-receive element, an acoustic lens disposed over an upper surface of the first substrate, and a damping layer disposed under the first substrate, wherein a second substrate is disposed between a lower surface of the first substrate and an upper surface of the damping layer, and the second substrate is made of a material having approximately the same linear expansion coefficient and acoustic impedance as the silicon substrate of the first substrate.

The examples of preferred specific structures according to the invention are as follows:

(1) The first substrate forms the transmit-receive element by providing an insulating layer, a gap, and an upper electrode over the silicon substrate which doubles as a lower electrode.

(2) In the above (1), the transmit-receive element is formed of the silicon substrate doubling as the lower electrode, a first insulating layer formed on an upper surface of the silicon substrate, a second insulating layer formed on an upper surface of the first insulating layer, plural the gaps formed between the first insulating layer and the second insulating layer, and plural the upper electrodes formed corresponding to the respective gaps within the second insulating layer.

(3) The first substrate forms the transmit-receive element by providing an insulating layer, a lower electrode, a gap, and an upper electrode over the silicon substrate.

(4) In the above (3), the transmit-receive element is formed of a first insulating layer formed on an upper surface of the silicon substrate, a second insulating layer formed on an upper surface of the first insulating layer, plural the gaps formed between the first insulating layer and the second insulating layer, plural the lower electrodes formed under the respective gaps within the second insulating layer, and plural the upper electrodes formed over the respective gaps within the second insulating layer.

(5) The first substrate and the second substrate are fixed through an adhesion layer, and the second substrate and the damping layer are fixed through another adhesion layer.

(6) The second substrate is made of aluminum nitride or 42 alloy.

(7) The insulating layer over the silicon substrate is made of at least one of silicon oxide and silicon nitride.

According to the invention, it is possible to achieve the ultrasound probe which can prevent damage to the silicon substrate due to temperature change and has excellent transmission/reception performance and structure reliability.

DESCRIPTION OF THE PREFERRED EMBODIMENTS

Figure 1:
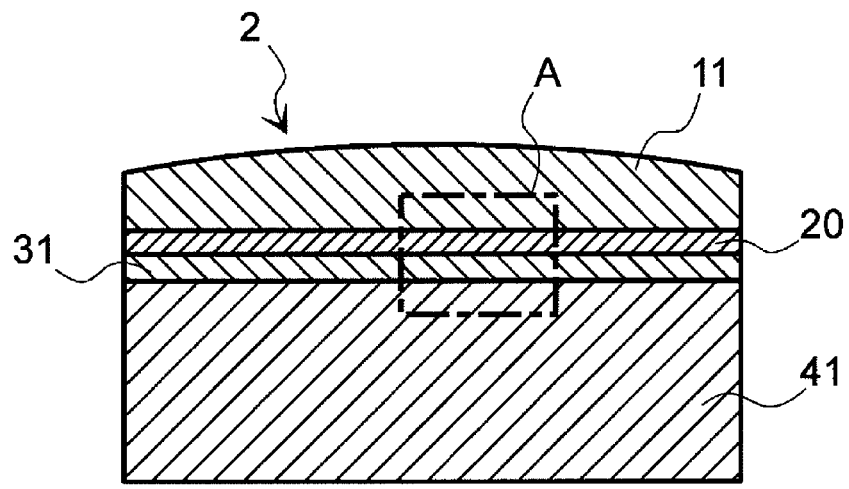
FIG. 1 is a sectional view of an ultrasound probe according to a first embodiment of the present invention.

Hereinafter, plural embodiments of the present invention will be described with reference to the accompanying drawings. In the drawings of the embodiments, same reference numerals denote same or similar parts.

First Embodiment

An ultrasound probe according to a first embodiment of the invention will be described with reference to FIGS. 1 to 3F.

Figure 2:
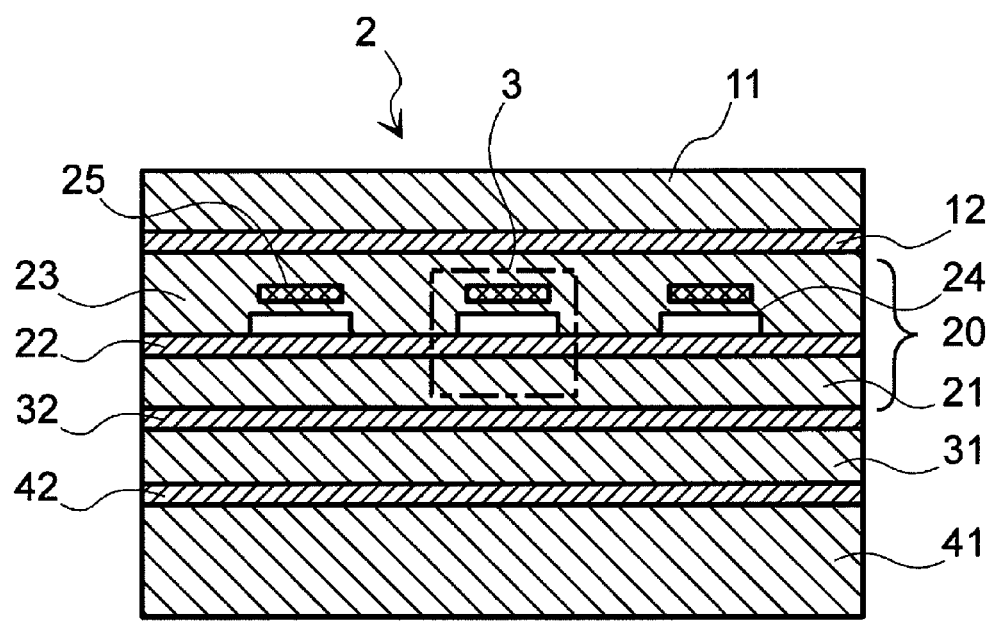
FIG. 2 is an enlarged view of an ultrasound transmit-receive element in FIG. 1.

FIG. 1 is a sectional view of an ultrasound probe 2 according to the first embodiment of the invention. FIG. 2 is an enlarged view of an ultrasound transmit-receive element 3 in FIG. 1. FIGS. 3A to 3F are explanatory views of the operational principle of the ultrasound transmit-receive element 3 in FIG. 2.

The ultrasound probe 2 is a linear-type ultrasound probe which is composed of a first substrate 20 having a silicon substrate 21 (see FIG. 2) and an ultrasound transmit-receive element A (see FIG. 2 for details), an acoustic lens 11 disposed over the upper surface of the first substrate 20, a damping layer 41 disposed under the first substrate 20, and a second substrate 31 disposed between the lower surface of the first substrate 20 and the upper surface of the damping layer 41, as shown in FIG. 1.

The damping layer 41 has the function of reducing the reflection of ultrasound waves in transmission and reception and attenuating ultrasound waves that passed. As shown in FIGS. 1 and 2, the damping layer 41 is formed sufficiently thicker than the first substrate 20 and the second substrate 31 and disposed as the bottom of the ultrasound probe 2. The damping layer 41 is made of a material, having approximately the same acoustic impedance as the silicon substrate 21, obtained by mixing tungsten particles into epoxy resin in order to attenuate ultrasound waves by multiple reflection, or made of ferrite rubber.

The second substrate 31 has the function of preventing damage to the silicon substrate 21 due to temperature change. As shown in FIG. 2, the second substrate 31 is formed with approximately the same thickness as the silicon substrate 21, or thicker than the silicon substrate 21, and disposed between the upper surface of the damping layer 41 and the lower surface of the first substrate 20. The second substrate 31 is made of aluminum nitride or 42 alloy which is a material having approximately the same linear expansion coefficient and acoustic impedance as the silicon substrate 21.

The first substrate 20 in FIG. 1 has the function of transmitting and receiving ultrasound waves. As shown in FIG. 2, the first substrate 20 is composed of the silicon substrate 21, a first insulating layer 22 formed on the silicon substrate 21, and a second insulating layer 23 containing plural gaps 24 and plural upper electrodes 25 over the first insulating layer 22, and is disposed between the acoustic lens 11 and the second substrate 31. Plural ultrasound transmit-receive elements 3 are formed in the first substrate 20.

The damping layer 41, the second substrate 31, the first substrate 20, and the acoustic lens 11 are fixed through adhesion layers 42, 32, and 12 therebetween respectively to be multi-layered in this order from bottom to top. The adhesion layers 42, 32, and 12 are made of epoxy resin.

An ultrasound transmit-receive element 3 is composed of the silicon substrate 21, the first insulating layer 22, the second insulating layer 23, a gap 24, and an upper electrode 25 so as to have the function of transmitting and receiving ultrasound waves. The ultrasound transmit-receive element 3 transmits and receives ultrasound waves by applying voltages between the silicon substrate 21 and the upper electrode 25 and vibrating the films (the second insulating layer 23, the upper electrode 25) over the gap 24. The silicon substrate 21, the first insulating layer 22, the second insulating layer 23, and the upper electrode 25 are multi-layered in this order from bottom to top.

The silicon substrate 21 is disposed over the upper surface of the second substrate 31 through the adhesion layer 32, and doubles as the lower electrode of the ultrasound transmit-receive elements 3. The first insulating layer 22 is disposed on the upper surface of the silicon substrate 21 which doubles as the lower electrode so as to ensure the insulation between the silicon substrate 21 and the upper electrodes 25. The thickness thereof ranges from 50 to 400 nm. The second insulating layer 23 is disposed on the upper surface of the first insulating layer 22. The second insulating layer 23 has recesses formed at the lower surface to form plural gaps 24 between the first insulating layer 22 and the second insulating layer 23, and embeds plural upper electrodes 25 over the respective gaps 24. The gap 24 ranges from 100 to 300 nm, and the thickness of the upper electrode 25 is 400 nm. Since the second insulating layer 23 forms the gaps 24 and embeds the upper electrodes 25, the second insulating layer 23 is thicker than the first insulating layer 22, and the thickness thereof is 2000 nm. In particular, the second insulating layer 23 has an effect on an acoustic pressure, a center frequency, and a fractional bandwidth which are the characteristics of the ultrasound transmit-receive element 3; accordingly, by adjusting it according to application, the ultrasound probe 2 can be applied to tests of various subjects. It is preferable that the first insulating layer 22 and the second insulating layer 23 are made of at least one of silicon nitride and silicon oxide. The upper electrodes 25 are located right above the respective gaps 24 and formed within the second insulating layer 23. It is preferable that the upper electrode 25 is made of aluminum, aluminum nitride, titanium nitride, or titanium.

The acoustic lens 11 has the function of matching the acoustic impedance to that of a test body (not shown) and focusing ultrasound waves. As shown in FIG. 2, the acoustic lens 11 is formed sufficiently thicker than the first substrate 20 and the second substrate 31 and disposed as the top of the ultrasound probe 2. The acoustic lens 11 is disposed over the upper surface of the second insulating layer 23 through the adhesion layer 12. The upper surface of the acoustic lens 11 is slightly curved upwardly, with the curvature differing according to the depth of focus on a subject, that is, detection application.

The operational principle of transmitting and receiving ultrasound waves by the ultrasound probe 2 with this structure will be described with reference to FIGS. 3A to 3F.

Figure 3A:
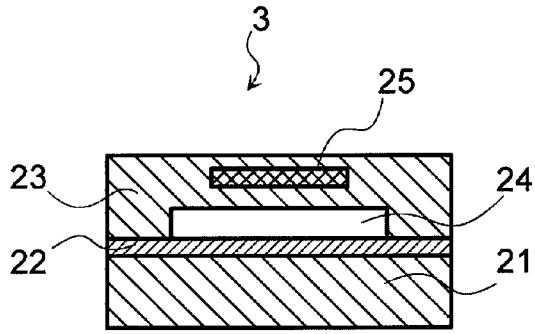
FIGS. 3A to 3F are explanatory views of the operational principle of the ultrasound transmit-receive element in FIG. 2.
Figure 3E:
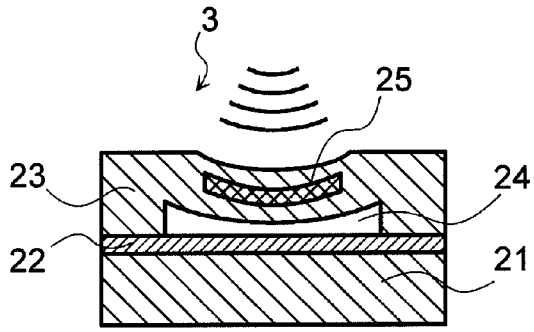
Figure 3B:
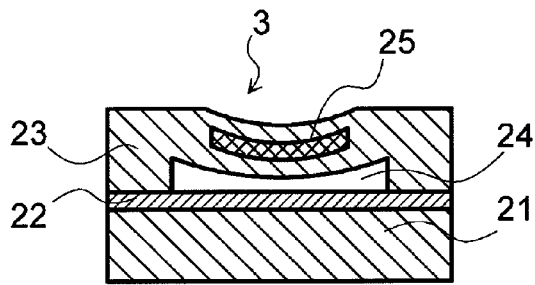
Figure 3F:
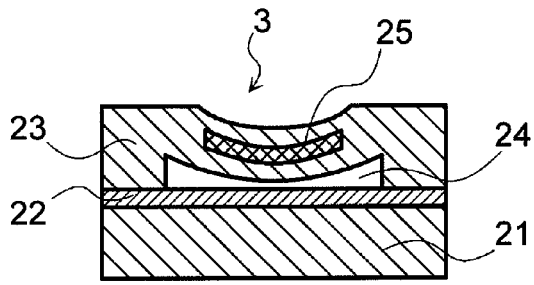
Figure 3C:
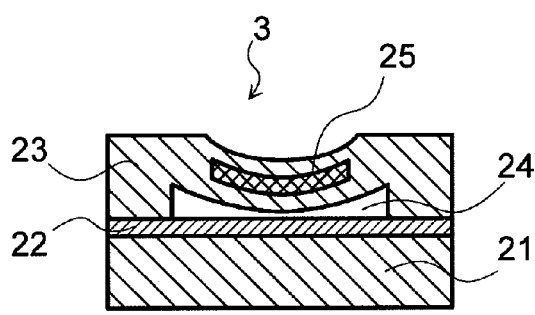
Figure 3D:
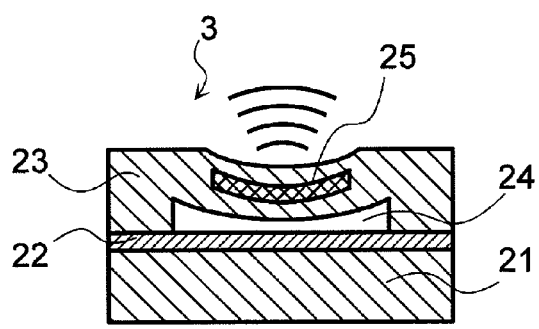

When the ultrasound transmit-receive element 3 transmits an ultrasound wave, in a state of FIG. 3A, a DC bias voltage is applied between the silicon substrate 21 doubling as the lower electrode and the upper electrode 25, thereby contracting the gap 24 to a predetermined position as shown in FIG. 3B. In this state, an AC voltage for transmitting an ultrasound wave is applied between the silicon substrate 21 doubling as the lower electrode and the upper electrode 25, thereby expanding and contracting the gap 24 to generate an ultrasound wave, as shown in FIGS. 3C and 3D. The ultrasound wave generated from the ultrasound transmit-receive element 3 in FIG. 1 is transmitted to a subject through the acoustic lens 11.

When the ultrasound transmit-receive element 3 receives an ultrasound wave, a DC bias voltage is applied between the silicon substrate 21 doubling as the lower electrode and the upper electrode 25, thereby shortening the gap 24 to a predetermined position. In this state, an ultrasound wave reflected from the subject expands and contracts the gap 24 as shown in FIGS. 3E and 3F, which changes the capacitance between the silicon substrate 21 and the upper electrode 25. Accordingly, by detecting this change, it is possible to detect the ultrasound wave.

In this embodiment, the linear expansion coefficient of the silicon substrate 21 is 3.5, and the acoustic impedance thereof is 21 kg/m$^2$s. The linear expansion coefficient of 42 alloy ranges from 4 to 5, and the acoustic impedance thereof is 47 kg/m$^2$s. The linear expansion coefficient of aluminum nitride is 3.7, and the acoustic impedance thereof is 34 kg/m²s. The linear expansion coefficient of the damping layer 41 is 100 or more, and the acoustic impedance thereof is 10 kg/m²s or less.

An ultrasound reflectance r by an acoustic impedance difference at the interface between two materials is expressed as: $r=(Z1-Z2)/(Z1+Z2)$. The reflectance r between the silicon substrate 21 and the damping layer 41 is 0.35. In the case where the second substrate 31 of aluminum nitride or 42 alloy is mounted between the silicon substrate 21 and the damping layer 41, the reflectance r between the silicon substrate 21 and the aluminum nitride 31 is 0.24 and the reflectance r between the silicon substrate 21 and the 42 alloy 31 is 0.38, which are similar to the reflectance r between the silicon substrate 21 and the damping layer 41. Further, the reflectance r between the aluminum nitride 31 and the damping layer 41 is 0.54 and the reflectance r between the 42 alloy 31 and the damping layer 41 is 0.64; however, in consideration of an ultrasound wave that passes through the interface between the silicon substrate 21 and the second substrate 31, the reflectance r in the case of using the aluminum nitride is 0.41 and the reflectance r in the case of using the 42 alloy is 0.39, which are similar to the reflectance of the damping layer 41. For example, assuming that an ultrasound wave emitted from the silicon substrate 21 is 1, since the reflectance at the interface between the silicon substrate 21 and the second substrate 31 is 0.24 (aluminum nitride) or 0.38 (42 alloy), an ultrasound wave that passes through the interface therebetween is 0.76 (aluminum nitride) or 0.62 (42 alloy). The reflectance at the interface between the second substrate 31 and the damping layer 41 is 0.76×0.54=0.41 (aluminum nitride) or 0.62×0.64=0.39 (42 alloy). On the other hand, since there is a great difference in linear expansion coefficient between the silicon substrate 21 and the damping layer 41, if the silicon substrate 21 and the damping layer 41 are directly bonded together, the structure reliability decreases due to temperature increase, which may cause stress concentration on the silicon substrate 21 and destroy it. For this reason, in this embodiment, the second substrate 31 of aluminum nitride or 42 alloy is mounted between the silicon substrate 21 and the damping layer 41, thereby making it possible to reduce the stress concentration on the silicon substrate 21 and greatly improve the structure reliability.

Even though the second substrate 31 is mounted between the silicon substrate 21 and the damping layer 41, since the reflectance r between the silicon substrate 21 and the damping layer 41 is small, ultrasound waves emitted behind the ultrasound transmit-receive element 3 can be efficiently propagated to the damping layer 41.

As described above, according to this embodiment, the second substrate 31 is disposed between the lower surface of the first substrate 20 and the upper surface of the damping layer 41, and the second substrate 31 is made of a material having approximately the same linear expansion coefficient and acoustic impedance as the silicon substrate 21 of the first substrate 20, thus making it possible to achieve the ultrasound probe 2 which can prevent damage to the silicon substrate 21 due to temperature change and has excellent transmission/reception performance and structure reliability.

Second Embodiment

Figure 4:
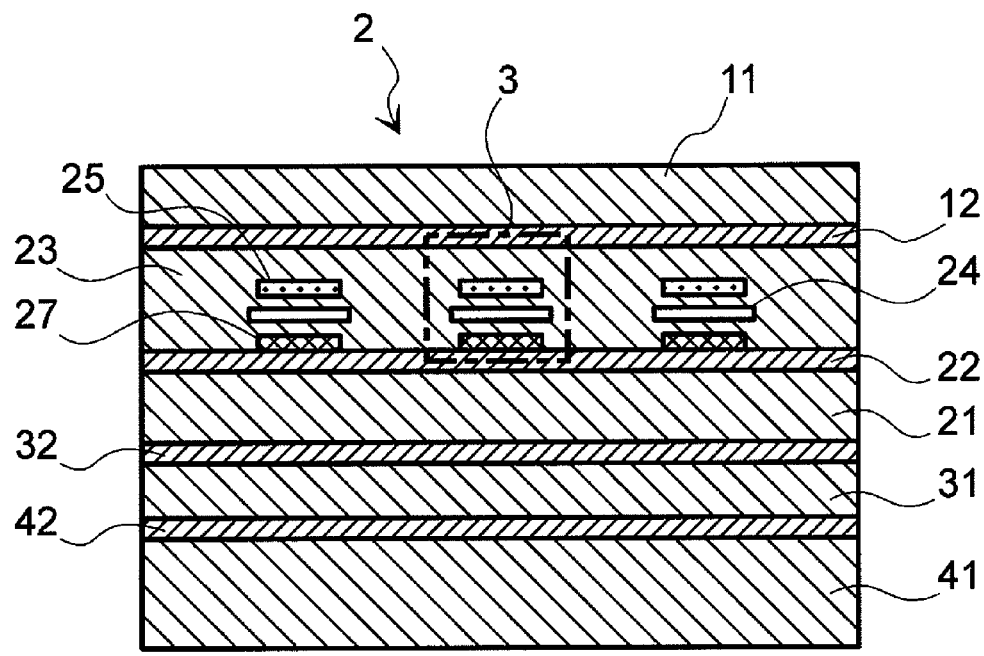
FIG. 4 is an enlarged view of an ultrasound transmit-receive element of an ultrasound probe according to a second embodiment of the invention.

Next, an ultrasound probe according to a second embodiment of the invention will be described with reference to FIG. 4. FIG. 4 is an enlarged view of the essential portion of the ultrasound probe according to the second embodiment of the invention. The second embodiment is different from the first embodiment in the following point and is basically the same as the first embodiment in the other points; therefore, repetitive description will be omitted.

In the second embodiment, plural ultrasound transmit-receive elements 3 are composed of the first insulating layer 22 formed on the upper surface of the silicon substrate 21, the second insulating layer 23 formed on the upper surface of the first insulating layer 22, plural gaps 24 formed within the second insulating layer 23, plural lower electrodes 27 formed on the upper surface of the first insulating layer 22 and under the respective gaps 24 through the second insulating layer 23, and plural upper electrodes 25 formed corresponding to the respective gaps 24 within the second insulating layer 23. The ultrasound transmit-receive element 3 is driven by applying voltages between an upper electrode 25 and a lower electrode 27 as described above. It is preferable that the lower electrode 27 is made of aluminum, aluminum nitride, or titanium nitride, as in the case of the upper electrode 25.

In this embodiment, unlike the first embodiment in which the silicon substrate doubles as the lower electrode, the lower electrodes 27 are disposed individually in the respective ultrasound transmit-receive elements, thus making it possible to individually drive the ultrasound transmit-receive elements 3.

Third Embodiment

Figure 5:
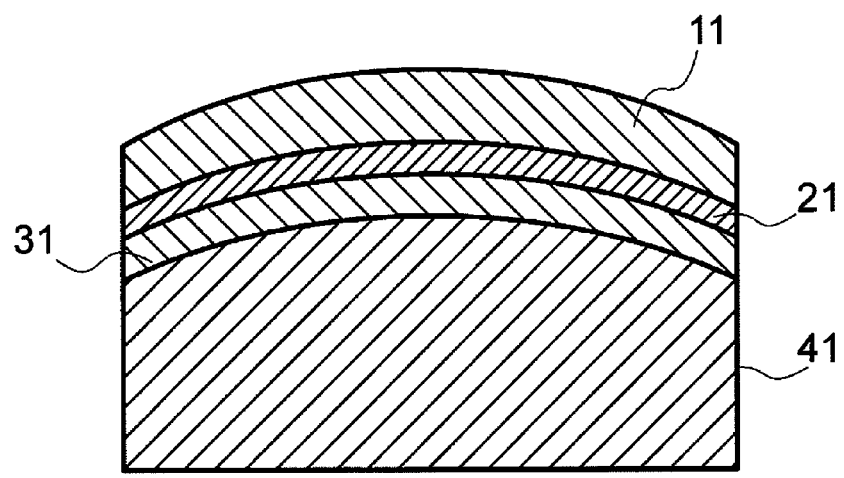
FIG. 5 is a sectional view of an ultrasound probe according to a third embodiment of the invention.

Next, a third embodiment of the invention will be described with reference to FIG. 5. FIG. 5 is an enlarged view of the essential portion of an ultrasound probe according to the third embodiment of the invention. The third embodiment is different from the first embodiment in the following point and is basically the same as the first embodiment in the other points; therefore, repetitive description will be omitted.

The ultrasound probe 2 according to the third embodiment has the structure of a convex-type ultrasound probe. The convex-type ultrasound probe 2 is composed of the silicon substrate 21 provided with the ultrasound transmit-receive elements 3 shown in FIG. 1, the second substrate 31, the damping layer 41, and the acoustic lens 11. The silicon substrate 21 and the second substrate 31 are curved with a predetermined curvature (e.g., 40 mm). Since the silicon substrate 21 is curved, it is preferable that the thickness thereof is not more than 50 μm. Since aluminum nitride which is a ceramic material is difficult to process, it is preferable that 42 alloy which is easy to process is used for the second substrate 31.

What is claimed is:
1. An ultrasound probe comprising:
a first substrate having a silicon substrate and an ultrasonic transmit-receive element;
an acoustic lens disposed over an upper surface of the first substrate; and
a damping layer disposed under the first substrate,
wherein a second substrate is disposed between a lower surface of the first substrate and an upper surface of the damping layer,
wherein the second substrate is made of a material having approximately the same linear expansion coefficient and acoustic impedance as the silicon substrate of the first substrate, and
wherein the first substrate forms the transmit-receive element by providing an insulating layer, a gap, and an upper electrode over the silicon substrate which doubles as a lower electrode,
wherein the transmit-receive element is composed of the silicon substrate doubling as the lower electrode, a first insulating layer formed on an upper surface of the silicon substrate, a second insulating layer formed on an upper surface of the first insulating layer, a plurality of the gaps formed between the first insulating layer and the second insulating layer, and a plurality of the upper electrodes formed corresponding to the respective gaps within the second insulating layer.

2. An ultrasound probe comprising:

a first substrate having a silicon substrate and an ultrasonic transmit-receive element;

an acoustic lens disposed over an upper surface of the first substrate; and a damping layer disposed under the first substrate, wherein a second substrate is disposed between a lower surface of the first substrate and an upper surface of the damping layer, wherein the second substrate is made of a material having approximately the same linear expansion coefficient and acoustic impedance as the silicon substrate of the first substrate, wherein the first substrate forms the transmit-receive element by providing an insulating layer, a lower electrode, a gap, and an upper electrode over the silicon substrate, and wherein the transmit-receive element is composed of a first insulating layer formed on an upper surface of the silicon substrate, a second insulating layer formed on an upper surface of the first insulating layer, a plurality of the gaps formed between the first insulating layer and the second insulating layer, a plurality of the lower electrodes formed under the respective gaps within the second insulating layer, and a plurality of the upper electrodes formed over the respective gaps within the second insulating layer.

3. The ultrasound probe according to claim 1 or claim 2, wherein the second substrate is made of aluminum nitride or 42 alloy.

4. The ultrasound probe according to claim 1 or claim 2, wherein the insulating layer over the silicon substrate is made of at least one of silicon oxide and silicon nitride.

5. The ultrasound probe according to claim 1 or claim 2, wherein the first substrate and the second substrate are fixed through an adhesion layer, and the second substrate and the damping layer are fixed through another adhesion layer.

\* \* \* \* \*